(12) United States Patent
Toth et al.

(10) Patent No.: US 7,593,761 B1
(45) Date of Patent: Sep. 22, 2009

(54) METHOD AND APPARATUS OF DETERMINING AND DISPLAYING AN ARTIFACT INDEX

(75) Inventors: Thomas L. Toth, Brookfield, WI (US); Piero Simoni, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 912 days.

(21) Appl. No.: 11/160,027

(22) Filed: Jun. 6, 2005

Related U.S. Application Data

(60) Continuation of application No. 10/065,450, filed on Oct. 18, 2002, now Pat. No. 6,983,180, which is a division of application No. 09/682,914, filed on Oct. 31, 2001, now Pat. No. 6,680,995.

(51) Int. Cl.
*A61B 6/00* (2006.01)

(52) U.S. Cl. .................. 600/407; 600/425; 378/4; 378/901; 382/131; 382/260

(58) Field of Classification Search ............... 600/407, 600/410, 425, 436, 437, 443; 382/128, 131, 382/132; 378/1, 4, 5, 21, 51, 54–56, 62
See application file for complete search history.

(56) References Cited

U.S. PATENT DOCUMENTS

| | | | |
|---|---|---|---|
| 5,602,891 A | 2/1997 | Pearlman | |
| 5,809,105 A | 9/1998 | Roehm et al. | |
| 5,818,896 A | 10/1998 | Hsieh | |
| 5,841,828 A | 11/1998 | Gordon et al. | |
| 6,023,494 A | 2/2000 | Senzig et al. | |
| 6,094,468 A | 7/2000 | Wilting et al. | |
| 6,115,487 A | 9/2000 | Toth et al. | |
| 6,115,489 A | 9/2000 | Gupta et al. | |
| 6,215,841 B1 | 4/2001 | Hsieh | |
| 6,222,642 B1 | 4/2001 | Farrell et al. | |
| 6,325,539 B1 | 12/2001 | Bromberg et al. | |
| 6,359,958 B2 | 3/2002 | Toth | |
| 6,366,638 B1 | 4/2002 | Hsieh | |
| 6,438,195 B1 | 8/2002 | Hsieh | |
| 6,480,560 B2 | 11/2002 | Hsieh | |
| 6,501,849 B1 | 12/2002 | Gupta et al. | |
| 6,529,574 B1 | 3/2003 | Hsieh | |
| 6,587,537 B1 | 7/2003 | Hsieh | |
| 6,600,802 B1 | 7/2003 | Hsieh | |
| 6,680,995 B2 | 1/2004 | Toth et al. | |
| 6,983,180 B2 * | 1/2006 | Toth et al. | 600/407 |
| 2002/0071600 A1 | 6/2002 | Yamada | |
| 2003/0083565 A1 | 5/2003 | Toth et al. | |

* cited by examiner

*Primary Examiner*—Brian Casler
*Assistant Examiner*—James Kish
(74) *Attorney, Agent, or Firm*—Ziolkowski Patent Solutions Group, SC

(57) ABSTRACT

An apparatus and process for determining and displaying an artifact index (AI) to a system operator are provided. The AI is determined by acquiring and processing imaging data of a phantom. The AI is then displayed to the operator on a console so that the operator may, if necessary, reset the scanning parameters or select a new scanning protocol that will result in a reconstructed image of a subject having reduced artifact presence. By providing a likelihood of artifact presence to the system operator, the present invention eliminates the need for the operator to recall those scanning profiles that are susceptible to high artifact presence.

32 Claims, 5 Drawing Sheets

METHOD AND APPARATUS OF DETERMINING AND DISPLAYING AN ARTIFACT INDEX

CROSS-REFERENCE TO RELATED APPLICATION

The present application is a continuation and claims priority of U.S. Ser. No. 10/065,450 filed Oct. 18, 2002 now U.S. Pat. No. 6,983,180 which is a divisional and claims priority of U.S. Ser. No. 09/682,914 filed Oct. 31, 2001 and entitled "Method and Apparatus of Determining and Displaying a Helical Artifact Index, now U.S. Pat. No. 6,680,995."

BACKGROUND OF THE INVENTION

The present invention relates generally to medical imaging and developing imaging protocols and, more particularly, to a method and apparatus to determine a likelihood of artifact presence in a reconstructed image and displaying the likelihood of artifact presence to an operator for evaluation. The present invention enables redevelopment and/or redesigning of the imaging protocol based upon the likelihood of artifact presence in a reconstructed image.

Typically, helical reconstruction algorithms produce artifacts in a reconstructed image due to data inconsistencies generated by a patient translation in a z direction during gantry rotation. While the intensity of artifacts depends in large part on the particular scanning parameters of the scanning session, generally these artifacts are most intense around high contrast interfaces such as bone/tissue (ribs) or air/tissue cavities. Additionally, artifact intensity typically increases with pitch but may also change depending upon the implemented helical reconstruction algorithm and detector width used to acquire imaging data.

With known imaging systems, it is incumbent upon the scanner operator to understand the artifact intensity with prescribing a patient examination. Typically, the operator learns from experience whether a particular scan procedure will result in an increased or decreased artifact presence. Moreover, the operator must be cognizant of scan versus artifact presence for a number of scanning possibilities without the benefit of any visual queues. While under some circumstances a large artifact presence in the final reconstructed image is not bothersome, for other scan procedures a reconstructed image absent visual artifacts is paramount.

For single slice CT systems that employ simple reconstruction weighting schemes, the scanning operators typically utilize the helical pitch of the scan as an indication of expected artifact. This can be difficult however for a new or inexperienced operator or for a CT system that has numerous operating modes. Furthermore, in multi-slice CT systems, with various pitch and detector width selections, an operator or technologist may find it very difficult to remember what to expect for each set of operating conditions.

Therefore, it would be desirable to design an apparatus and method that determines and visually displays a likelihood of artifact presence in a reconstructed image for evaluation by a scan system operator. Further, it would be desirable to design such a system that enables the system operator to provide feedback to the system such that artifact presence is reduced in a subsequent imaging session.

BRIEF DESCRIPTION OF THE INVENTION

An apparatus and process overcoming the aforementioned drawbacks is provided and includes determining and displaying a helical artifact index (HAI) to a system operator. The HAI is determined by acquiring and processing imaging data of a phantom. The HAI is then displayed to the operator on a console so that the operator may, if necessary, reset the scanning parameters or select a new scanning protocol that will result in a reconstructed image of a patient having reduced artifact presence. By providing a likelihood of artifact presence to the system operator, the present invention eliminates the need for the operator to recall those scanning profiles that are susceptible to high artifact presence.

Therefore, in accordance with one aspect of the present invention, a method of generating a helical artifact score is provided. The method includes acquiring a set of data values and setting a subset of the set of data values to an initial value. After setting the subset of data values to an initial value, the method includes filtering the set of data values. Next, a likelihood of artifact presence is determined from the filtered set of data values.

In accordance with another aspect of the present invention, a computer-readable medium having stored thereon a computer program that, when executed by one or more computers, causes the one or more computers to acquire imaging data of a phantom from an external device. The imaging data includes a plurality of pixels. The computer program further causes the one or more computers to isolate a first set and a second set of pixels and set one of the first set and the second set to an initial value. After setting one of the first set and the second set to an initial value, the computer program causes the one or more computers to filter the imaging data and determine a helical artifact index (HAI) therefrom. The computer program then causes the one or more computers to visually display the HAI on a console.

In yet another aspect of the present invention, a CT system is provided and comprises a rotatable gantry having an opening and a high frequency electromagnetic energy projection source to project high frequency energy toward an object. The CT system further includes a scintillator array having a plurality of scintillators to receive high frequency electromagnetic energy attenuated by the object. A photodiode array is provided having a plurality of photodiodes. The photodiode array is optically coupled to the scintillator array and is configured to detect light energy emitted therefrom. The CT system further includes a plurality of electrical interconnects configured to transmit photodiode outputs to a data processing system and a computer program to acquire and process data to determine a likelihood of an artifact risk presence in a reconstructed image. The computer of the CT system is further programmed to notify an operator of the determined likelihood.

Various other features, objects and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

The operating environment of the present invention is described with respect to a four-slice computed tomography (CT) system. However, it will be appreciated by those of ordinary skill in the art that the present invention is equally applicable for use with single-slice or other multi-slice configurations. Additionally, the present invention is applicable for use with a CT scanner, an MRI scanner, an x-ray scanner, a PET imaging system, or an ultrasound imaging system, for example. Moreover, the present invention will be described with respect to the detection and conversion of x-rays. However, one of ordinary skill in the art will further appreciate, that the present invention is equally applicable for the detection and conversion of other high frequency electromagnetic energy.

Figure 1:
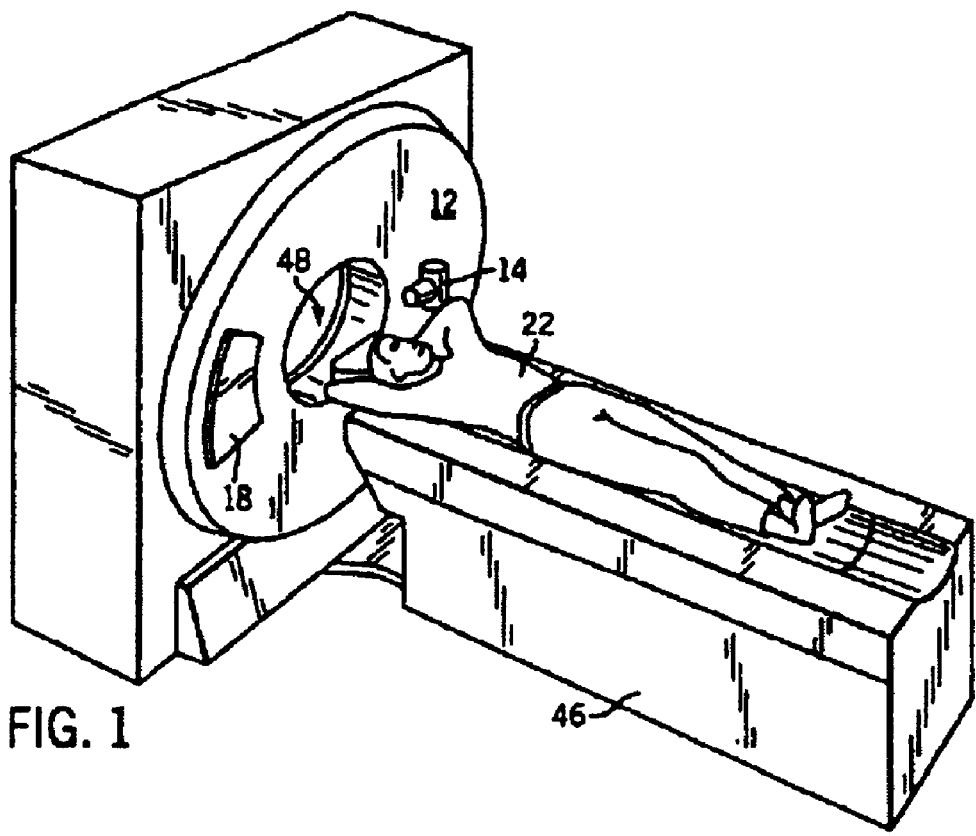
FIG. 1 is a pictorial view of a CT imaging system.
Figure 2:
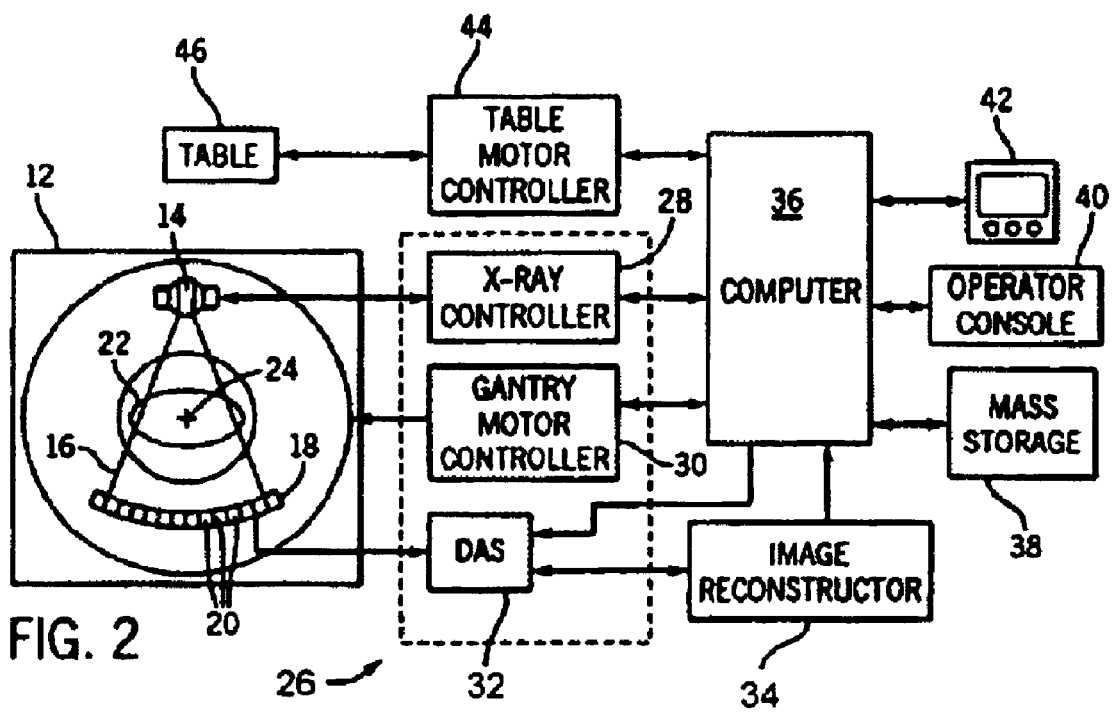
FIG. 2 is a block schematic diagram of the system illustrated in FIG. 1.

Referring to FIGS. 1 and 2, an exemplary computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of the gantry 12. Detector array 18 is formed by a plurality of detectors 20 which together sense the projected x-rays that pass through a medical patient 22. Each detector 20 produces an electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. A data acquisition system (DAS) 32 in control mechanism 26 samples analog data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves portions of patient 22 through a gantry opening 48.

Figure 3:
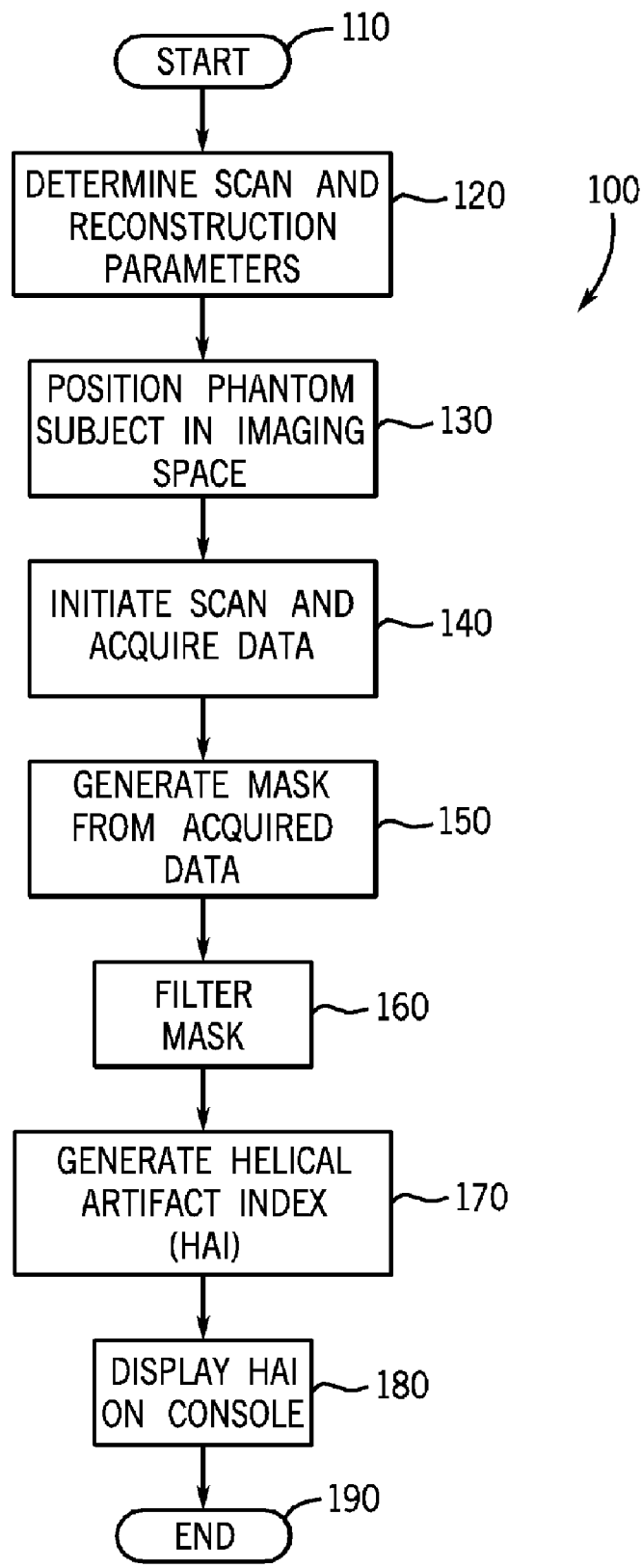
FIG. 3 is a flow chart setting forth the steps of displaying a likelihood of artifact presence in a reconstructed image in accordance with the present invention.

Referring to FIG. 3, a process 100 for acquiring imaging data of a phantom and displaying a helical artifact index (HAI) of a reconstructed image based on the acquired imaging data of the phantom is shown. The process 100 begins at 110 with the prescription of an imaging scan for a subject such as a medical patient by a scan operator or other healthcare provider. At 120, a system operator determines scan and reconstruction parameters necessary to satisfy the prescription prescribed at 110. Once the scan and reconstruction parameters are determined at 120, a phantom is positioned in an imaging space. The present invention is applicable with any phantom designed to simulate an anatomical region of a subject. For example, the phantom may include an anthropomorphic shaped helical body phantom (HBP) having an elliptical shape and having diagonal rods at the periphery to simulate ribs of a subject. Other phantoms may also be implemented that simulate other anatomical regions such as, a heart, brain, tissue, etc.

After the phantom is positioned in the imaging space at 130, a scan is initiated and imaging data is acquired at 140 in accordance with the scan parameters defined at 120. A mask is then generated at 150 from the acquired data and filtered at 160. In a preferred embodiment, the mask is generated by identifying those pixels of the acquired imaging data within ±40 CT numbers of an expected uniform material value. This is accomplished by measuring the mean for a region of pixels near the center of the phantom absent any visual artifact.

After the mask is filtered at 160, process 100 generates a helical artifact index (HAI) at 170 as will be discussed with particular reference to FIG. 4. The HAI is then displayed on a console at 180 whereupon process 100 ends at 190.

Figure 4:
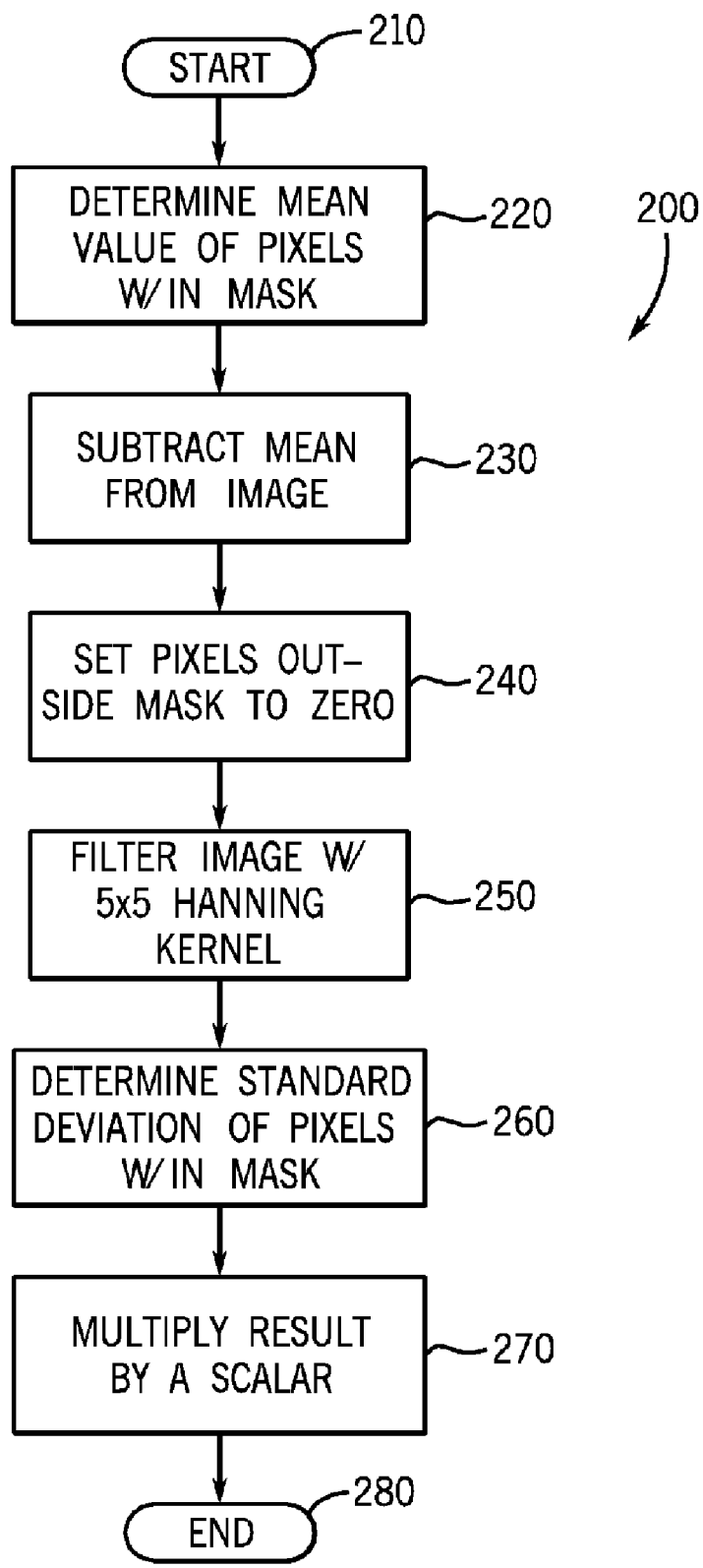
FIG. 4 is a flow chart setting forth the steps of determining a likelihood of artifact presence.

Referring to FIG. 4, an algorithm 200 for determining the HAI begins at 210 with the determining of a mean value of pixels within the mask at 220. The mean value of the pixels within the mask is then subtracted from the image at 230. At 240, the pixels outside the mask are then set to an initial value. In one preferred embodiment, the initial value is zero. This however is illustrative of only one preferred embodiment. That is, the present invention is applicable with non-zero initial values.

After the pixels outside the mask are set to an initial value 240, the imaging data acquired at 140, FIG. 3, is filtered, in a preferred embodiment, with a 5×5 Hanning kernel. An illustrative 5×5 Hanning kernel applicable with the present invention is set forth in the table below.

TABLE 1

| 0.00000 | 0.00000 | 0.00000 | 0.00000 | 0.00000 | 0.00000 | 0.00000 |
| 0.00000 | 0.00694444 | 0.0208333 | 0.0277778 | 0.0208333 | 0.00694445 | 0.00000 |
| 0.00000 | 0.0208333 | 0.0625000 | 0.0833333 | 0.0625000 | 0.0208333 | 0.00000 |
| 0.00000 | 0.0277778 | 0.0833333 | 0.111111 | 0.0833333 | 0.0277778 | 0.00000 |
| 0.00000 | 0.0069445 | 0.0208333 | 0.0277778 | 0.028333 | 0.0069445 | 0.00000 |
| 0.00000 | 0.00694445 | 0.0208333 | 0.0277778 | 0.0208333 | 0.00694445 | 0.00000 |
| 0.00000 | 0.00000 | 0.00000 | 0.00000 | 0.00000 | 0.00000 | 0.00000 |

After the imaging data is filtered at 250, a standard deviation of the pixels within the mask is determined at 260. The standard deviation is determined by squaring the pixels within the mask, summing the squares, and dividing the sum by the total number of pixels within the mask. At 270, the standard deviation is then multiplied by a scalar suitable to obtain a maximum score of 10 for the worst case of artifact presence in a reconstructed image and a minimum score of 1 for the best case of artifact risk over the set of parameters available to the user. Setting a worst case score to 10 and a best case score to 1 is illustrative of only one embodiment that may be used to ascertain an artifact risk value. That is, a best case score of 10 and a worst case score of 1 or any variation thereof is contemplated herein and is within the scope of the present invention. Process 200 then ends at 280 with the visual displaying of the artifact risk value, in a preferred embodiment, as a visual bar graph on a scan Rx console at 180 of FIG. 3 as was heretofore discussed.

Figure 5:
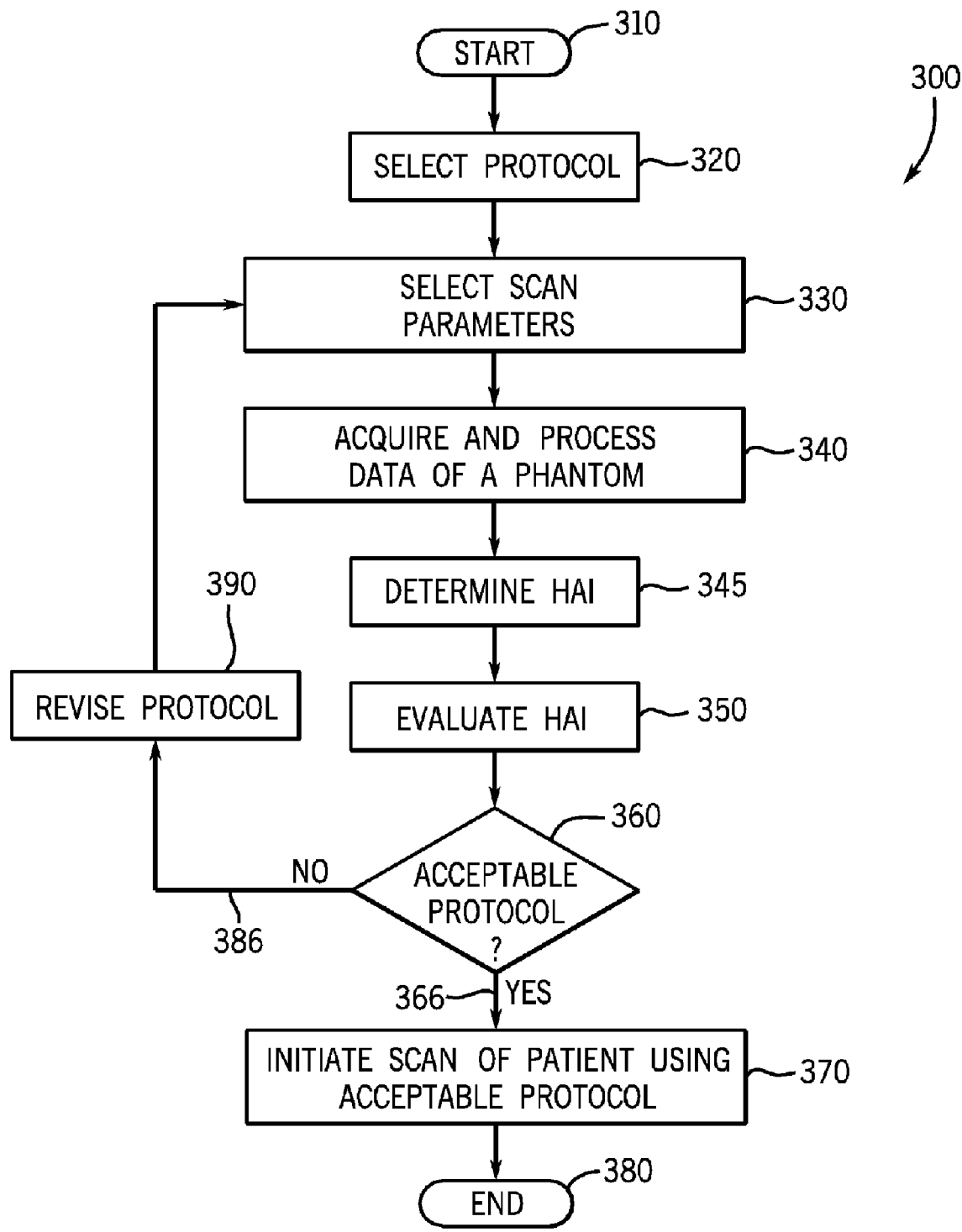
FIG. 5 is a flow chart setting forth the steps of a scanning session in accordance with the present invention.

Referring to FIG. 5, algorithm 300 sets forth the steps of an acquisition, pre-processing, and reconstruction process in accordance with the present invention. Algorithm 300 begins at 310 with the selection of a scanning protocol at 320. Once the appropriate protocol is selected at 320, scan parameters are identified and selected at 330 that satisfy the requirements of the prescribed imaging session. Imaging data is then acquired and processed of a phantom at 340 whereupon an HAI index is determined at 345 in accordance with acts 110-190 of process 100, FIG. 3. The determined HAI is then evaluated by the system operator at 350 to determine if the implemented protocol selected at 320 is acceptable 360. That is, if the HAI indicates a high likelihood of artifact presence and such a presence is unacceptable, the operator may determine at 360 that the protocol is unacceptable. However, if the artifact presence is low or that a high artifact presence is tolerable, the operator may determine that the protocol selected and implemented at 320 is acceptable.

If the protocol is acceptable 360, 366, the pre-processing process is complete and a scan of a patient using the acceptable protocol is executed at 370 whereupon algorithm 300 concludes at 380 with the reconstruction of an image. However, if the system operator determines at 360 that the protocol was not acceptable 386, the pre-processing process continues at 390 with a revising of the protocol at 390. Revising the reconstruction protocol allows the system operator to alter the reconstruction algorithm used to process the data or select new scan parameters at 330 that will facilitate image reconstruction with minimal artifact presence. Once the protocol is revised at 390 and, if necessary, new scan parameters are selected at 330, pre-processing continues at 340 with the acquisition and processing of data of a phantom and subsequent HAI determination and evaluation at 345 and 350. These pre-processing steps continue until an acceptable protocol is determined at 360. That is, regeneration of an HAI during pre-processing allows the system to provide visual feedback in the form of a bar graph to the operator so that a correct protocol may be selected and implemented.

Figure 6:
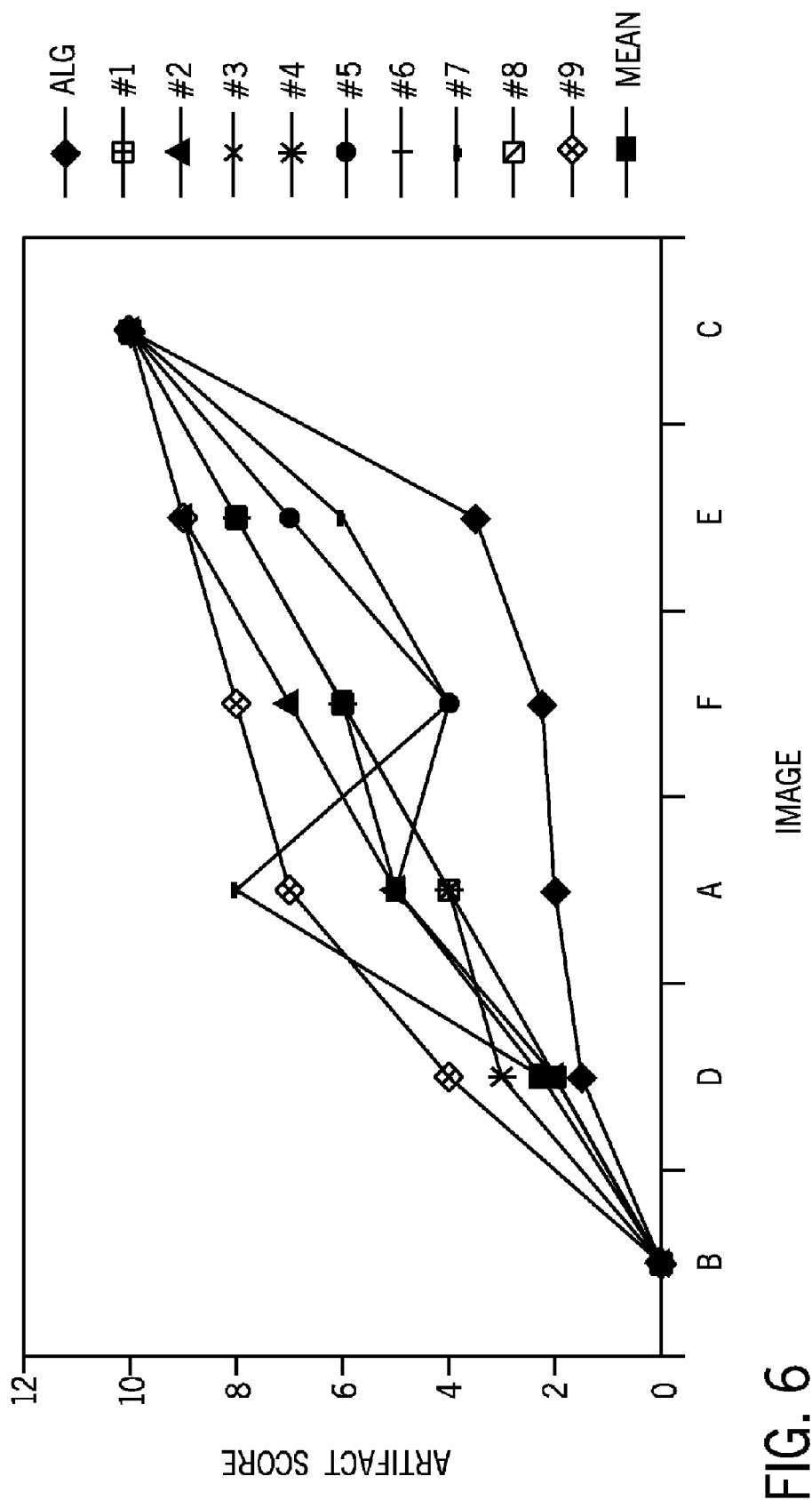
FIG. 6 is a histogram correlating the assignment of artifact presence values by the process of the present invention versus artifact value assignment by skilled observers.

Referring to FIG. 6, a histogram illustrating a comparison of artifact score assessment of the process of the present invention versus artifact score assessment by human observers is shown. That is, a set of helical body phantom images were evaluated using the helical artifact index generation process of the instant application. Those images were then presented to a set of skilled observers who were asked to sort and grade the images on a scale of 1 to 10 ranging from best to worst. As shown in FIG. 6, the artifact index generation process of the instant application scored the images in the same sequence as the skilled human observers thereby confirming that the helical artifact index generation process of the instant application correctly assigned index values to the images presented to the skilled observers.

Therefore, in accordance with one embodiment of the present invention, a method of generating a helical artifact score is provided. The method includes acquiring a set of data values and setting a subset of the set of data values to an initial value. After setting the subset of data values to an initial value, the method includes filtering the set of data values. Next, a likelihood of artifact presence is determined from the filtered set of data values.

In accordance with another embodiment of the present invention, a computer-readable medium having stored thereon a computer program that, when executed by one or more computers, causes the one or more computers to acquire imaging data of a phantom from an external device. The imaging data includes a plurality of pixels. The computer program further causes the one or more computers to isolate a first set and a second set of pixels and set one of the first set and the second set to an initial value. After setting one of the first set and the second set to an initial value, the computer program causes the one or more computers to filter the imaging data and determine a helical artifact index (HAI) therefrom. The computer program then causes the one or more computers to visually display the HAI on a console.

In yet another embodiment of the present invention, a CT system is provided and comprises a rotatable gantry having an opening and a high frequency electromagnetic energy projection source to project high frequency energy toward an object. The CT system further includes a scintillator array having a plurality of scintillators to receive high frequency electromagnetic energy attenuated by the object. A photodiode array is provided having a plurality of photodiodes. The photodiode array is optically coupled to the scintillator array and is configured to detect light energy emitted therefrom. The CT system further includes a plurality of electrical interconnects configured to transmit photodiode outputs to a data processing system and a computer program to acquire and process data to determine a likelihood of an artifact risk presence in a reconstructed image. The computer of the CT system is further programmed to notify an operator of the determined likelihood.

The present invention has been described in terms of the preferred embodiment, and it is recognized that equivalents, alternatives, and modifications, aside from those expressly stated, are possible and within the scope of the appending claims.

What is claimed is:

1. A computer readable medium having stored thereon a computer program that, when executed by a computer, causes the computer to:
   reconstruct an image comprising a plurality of pixels from imaging data acquired from an object;
   isolate a first set and a second set of pixels in the image;
   set the first set of pixels to an initial value;
   thereafter, filter the imaging data;
   determine an artifact index (AI); and
   visually display the AI on a console.

2. The computer readable medium of claim 1 wherein the program, in causing the computer to reconstruct the image, causes the computer to reconstruct the image comprising a plurality of pixels from imaging data acquired from the object, the imaging data comprising data acquired from the object via one of a CT scanner, an MRI scanner, an x-ray scanner, a PET imaging system, and an ultrasound imaging system.

3. The computer readable medium of claim 1 wherein the program, in causing the computer to reconstruct the image, causes the computer to reconstruct an image comprising a plurality of pixels from imaging data acquired from an object that has a shape to simulate an anatomical region of a patient.

4. The computer readable medium of claim 3 wherein the program, in causing the computer to reconstruct the image, causes the computer to reconstruct an image comprising a plurality of pixels from imaging data acquired from an object that has a shape to simulate a bone region.

5. The computer readable medium of claim 4 wherein the program, in causing the computer to reconstruct the image, causes the computer to reconstruct an image comprising a plurality of pixels from imaging data acquired from an object that has a shape to simulate a rib.

6. The computer readable medium of claim 3 wherein the program, in causing the computer to reconstruct the image, causes the computer to reconstruct an image comprising a plurality of pixels from imaging, data acquired from an object that has a shape to simulate tissue.

7. The computer readable medium of claim 1 wherein the computer program that causes the computer to the first set of pixels to an initial value further causes the computer to set the first set of pixels to zero.

8. The computer readable medium of claim 1 wherein the computer program further causes the computer to determine a mean of the second set of pixels.

9. The computer readable medium of claim 8 wherein the computer program further causes the computer to subtract the mean from the imaging data.

10. The computer readable medium of claim 1 wherein the computer program further causes the computer to:
square each pixel of the second set of pixels;
sum the squares;
divide the sum by a number of pixels of the second set of pixels; and
modify the quotient by a scalar.

11. The computer readable medium of claim 1 wherein the second set of pixels includes imaging values within ±40 CT numbers of a range of an expected uniform material value.

12. The computer readable medium of claim 1 wherein the second set of pixels includes pixels having no visual artifact.

13. The computer readable medium of claim 1 wherein the computer program further causes the computer to display the AI on the console as at least one of a histogram and a bar graph.

14. A method of generating an artifact score, the method comprising:
reconstructing an image having a plurality of pixels from imaging data acquired from a subject;
partitioning the plurality of pixels into a first set and a second set;
initializing the first set to a base value;
determining an artifact index (AI) from at least one of the first set and the second set; and
visually conveying the AI.

15. The method of claim 14 wherein the step of partitioning includes the step of generating a mask from the plurality of pixels.

16. The method of claim 15 wherein the step of generating a mask further comprises the step of identifying a set of pixels within a range of an expected uniform material value.

17. The method of claim 16 wherein the range is ±40 CT numbers.

18. The method of claim 16 wherein the step of identifying the set of pixels comprises isolating a region of the plurality of pixels absent visual artifacts.

19. The method of claim 16 further comprising the step of determining a numeric mean of the set of pixels within the range.

20. The method of claim 19 further comprising the step of subtracting the mean from each pixel of the plurality of pixels.

21. The method of claim 16 further comprising steps of:
squaring each pixel of the plurality of pixels;
summing the squared pixels; and
dividing the summation by a mask pixel count.

22. The method of claim 21 further comprising the step of modifying the quotient by a scalar.

23. The method of claim 22 further comprising the step of determining the scalar by statistically correlating trained observers responses to a reconstructed image of the imaging data.

24. The method of claim 22 wherein the step of determining an artifact index includes the step of determining a likelihood of artifact presence in the reconstructed image by comparing the modified quotient to an artifact scale.

25. The method of claim 24 wherein the artifact scale has a maximum of ten and a minimum of one.

26. The method of claim 14 further comprising the step of filtering the imaging data with a two-dimensional array.

27. The method of claim 26 wherein the filtering two dimensional array includes a Hanning kernel.

28. The method of claim 26 wherein the filtering two dimensional array has a five by five orientation.

29. The method of claim 14 wherein the base value is a whole number.

30. The method of claim 29 wherein the base value is zero.

31. The method of claim 14 wherein the subject includes a phantom designed to simulate an anatomical region of a patient.

32. The method of claim 14 wherein the step of reconstructing an image having a plurality of pixels from imaging data acquired from the subject comprises acquiring the imaging data from a phantom using a CT scanner.

* * * * *

UNITED STATES PATENT AND TRADEMARK OFFICE
CERTIFICATE OF CORRECTION

PATENT NO. : 7,593,761 B1
APPLICATION NO. : 11/160027
DATED : September 22, 2009
INVENTOR(S) : Toth et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1143 days.

Signed and Sealed this

Twenty-eighth Day of September, 2010

David J. Kappos
*Director of the United States Patent and Trademark Office*